United States Patent [19]

Delphis

[11] Patent Number: 6,150,538
[45] Date of Patent: Nov. 21, 2000

[54] PROCESS FOR MANUFACTURING CIS-ISOAMBRETTOLIDE AND USE THEREOF

[75] Inventor: Claude Delphis, Les Ulis, France

[73] Assignee: Synarome, Chartres, France

[21] Appl. No.: 09/250,645

[22] Filed: Feb. 16, 1999

[30] Foreign Application Priority Data

Feb. 20, 1998 [FR] France .................................. 98 02101

[51] Int. Cl.[7] .................................................. C07D 313/00
[52] U.S. Cl. ............................................................ 549/266
[58] Field of Search ............................................. 549/266

[56] References Cited

U.S. PATENT DOCUMENTS 2,417,151  3/1947  Collaud et al. .
4,014,902  3/1977  Tseng ................................... 260/340.9

OTHER PUBLICATIONS

Chemical Abstracts, vol. 98, No. 13, 1983 "Synthesis of Trans Delta9–Isoambrettolide" Majee et al., pp. 578.

*Primary Examiner*—Joseph McKane
*Assistant Examiner*—Taofiq A. Solola
*Attorney, Agent, or Firm*—Perman & Green, LLP

[57] ABSTRACT

Manufacture of a molecule which is of important olfactory interest for perfumers. This molecule belongs to the group of macrocyclic lactones with a musk odor. The manufacturing process consists in preparing cis-16-hydroxy-9-hexadecenoic acid or an ester of this acid, which is a precursor of cis-isoambrettolide, the latter being obtained by macrolactonization in a very high degree of purity. Use as a fragrance material.

16 Claims, 3 Drawing Sheets

PROCESS FOR MANUFACTURING CIS-ISOAMBRETTOLIDE AND USE THEREOF

BACKGROUND OF THE INVENTION

1. Field of the Invention

The present invention relates to a process for manufacturing cis-isoambrettolide in a very high degree of purity.

2. Description of the Prior Art

It is known that substances with a musk odor are commonly used in the perfume industry in the broad sense, where they have a primary advantage, both in the perfumes sector and in that of washing products such as soaps and detergents, on account of their persistent effect.

These molecules are represented by 4 families: the non-nitro aromatic musks, the nitro aromatic musks, the macrocyclic ketones and the macrocyclic lactones. The lactones are important aromatic agents on account of their abundance in natural products.

Among the macrocyclic lactones of natural origin, derived from the plant kingdom, mention may be made of exaltolide, of formula (1) and ambrettolide, of formula (2).

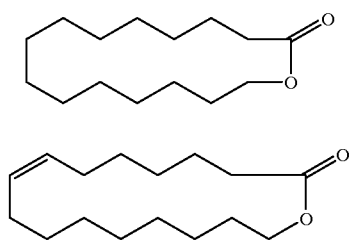

Ambrettolide is obtained from the essential oil and the resinoids of ambrette, whose round, warm, musk note is highly appreciated in perfumery. This plant is Hibiscus abelmoschus 4, which is grown in South America, Indonesia and the West Indies.

An unsaturated macrocyclic lactone is already known: trans-isoambrettolide of formula (3), which is obtained industrially, this being a geometrical and positional isomer of natural ambrettolide. A process for obtaining the trans lactone is described in U.S. Pat. No. 4,014,902.

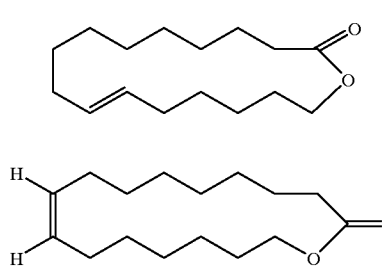

SUMMARY OF THE INVENTION

The present invention relates, however, to a process for manufacturing another geometrical and positional isomer of natural ambrettolide: cis-isoambrettolide of formula (4), which has the advantage of being much more powerful than trans-isoambrettolide in olfactory terms, thereby allowing it to be used in the perfume industry at much lower concentrations, resulting in considerable savings which make it all the more-appreciated.

In addition, the advantage of the process which is the subject of the present invention lies in the fact that it gives cis-isoambrettolide in a degree of purity of greater than 99.5%, this advantage being combined with the one above.

cis-16-Hydroxy-9-hexadecenoic acid is an essential chemical compound as a starting material for the synthesis of the macrocyclic lactone cis-isoambrettolide, of which it is the direct precursor.

The present invention thus relates to a process for manufacturing cis-16-hydroxy-9-hexadecenoic acid in order subsequently to obtain cis-isoambrettolide by the usual macrolactonization methods.

The present invention relates more particularly to a process for manufacturing cis-isoambrettolide, using the following chemical reaction steps:

a) trans-epoxidation of trans-16-hydroxy-9-hexadecenoic acid, of formula (5), which may or may not be esterified, to give the epoxide of formula (6);

b) opening of the epoxide bridge, to give erythro-aleuritic acid, or an ester of this acid, of formula (7);

c) action of an ortho ester of formula $HC(OR^3)_3$ on erythro-aleuritic acid, or its ester, to give the dioxolane of formula (9);

d) pyrolysis of the dioxolane to give cis-16-hydroxy-9-hexadecenoic acid, or an ester of this acid, of formula (10), in a purity of greater than 99%;

e) macrolactonization of the above acid, or its ester, resulting in cis-isoambrettolide.

A subject of the present invention is also, as a variant, a process for manufacturing cis-isoambrettolide, using the following chemical reaction steps:

a) trans-epoxidation of trans-16-hydroxy-9-hexadecenoic acid, of formula (5), which may or may not be esterified, to give the epoxide of formula (6);

b) opening of the epoxide bridge to give a mixture of β-hydroxy ethers of formula (8);

c) action of an ortho ester of formula $HC(OR^3)_3$ on the mixture of β-hydroxy ethers, to give the dioxolane of formula (9);

d) pyrolysis of the dioxolane to give cis-16-hydroxy-9-hexadecenoic acid, or an ester of this acid, of formula (10), in a purity of greater than 99%;

e) macrolactonization of the above acid, or its ester, resulting in cis-isoambrettolide.

In the above formulae:

$R^1$ represents a hydrogen atom or an acetyl radical, $R^2$ represents a hydrogen atom or a methyl radical, R represents a hydrogen atom or a methyl radical, R' represents a methyl radical or an ethyl radical, $R^3$ represents a methyl radical or an ethyl radical.

The examples which follow, which are given as guides, of one embodiment will further illustrate the 4 process for manufacturing cis-isoambrettolide according to the invention, without, however, limiting its scope.

The steps for preparing cis-16-hydroxy-9-hexadecenoic acid, the direct precursor of cis-isoambrettolide, are as follows:

a) preparation of the epoxide of formula (6) from trans-16-hydroxy-9-hexadecenoic acid, which may or may not be esterified, of formula (5), which is treated with hydrogen peroxide in a carboxylic acid medium such as formic acid or acetic acid, to give, via transepoxidation, the epoxide of formula (6);

b) opening of the epoxide bridge, by in situ hydrolysis, in acid or basic medium, of the epoxide, to give erythro-aleuritic acid or an ester of this acid, of formula (7);

b') as a variant, opening of the epoxide bridge, by alcoholysis of the epoxide, which gives a mixture of β-hydroxy ethers of formula (8);

c) production of the dioxolane of formula (9) by the action of an ortho ester of formula $HC(OR^3)_3$, on erythro-aleuritic acid or its ester;

c') as a variant, production of the dioxolane by the action of an ortho ester of formula $HC(OR^3)_3$ on the mixture of β-hydroxy ethers;

d) production of cis-16-hydroxy-9-hexadecenoic acid or its ester, of formula (10), by pyrolysis, in the presence or absence of solvent, of the dioxolane.

cis-Isoambrettolide is finally obtained by macrolactonization of its precursor acid.

EXAMPLE 1

Production of cis-isoambrettolide a) Preparation of erythro-aleuritic acid 350 ml of 30% hydrogen peroxide and 280 ml of formic acid are loaded into a 2-liter reactor fitted with a stirrer and an external condenser. The temperature of the mixture is lowered to 0° C.

500 g of trans-16-hydroxy-9-hexadecenoic acid are then added, at a rate such that the temperature of the mixture does not exceed 5° C. The temperature is then adjusted to 10° C. The mixture is kept stirring until total conversion, as indicated by chromatography, of the alkene.

The mixture is then diluted with 1 liter of water. It is then left to return to room temperature and stirring is continued for an additional day.

An acid-base extraction of the erythro-aleuritic acid is then carried out. Finally, this acid is purified by crystallization.

It will be noted that if an erythro-aleuritic acid ester is obtained, it will be purified by distillation.

b) Preparation of 16-hydroxyhexadecenoic acid

The acid or ester obtained above is treated at reflux with an ortho ester, which may be trimethyl orthoformate or triethyl orthoformate, until total conversion is obtained, as indicated by chromatography.

The in situ pyrolysis of the dioxolane thus obtained is then carried out, in the presence or absence of a solvent, which may be toluene or xylene, by raising the temperature to 160° C.

The ω-hydroxy acid or the ω-hydroxy ester thus obtained (cis-16-hydroxy-9-hexadecenoic acid or an ester of said acid) is purified by distillation.

c) Production of cis-isoambrettolide

The acid, or its ester, obtained above is treated under the usual macrolactonization conditions, to give cis-isoambrettolide.

Figure 1:
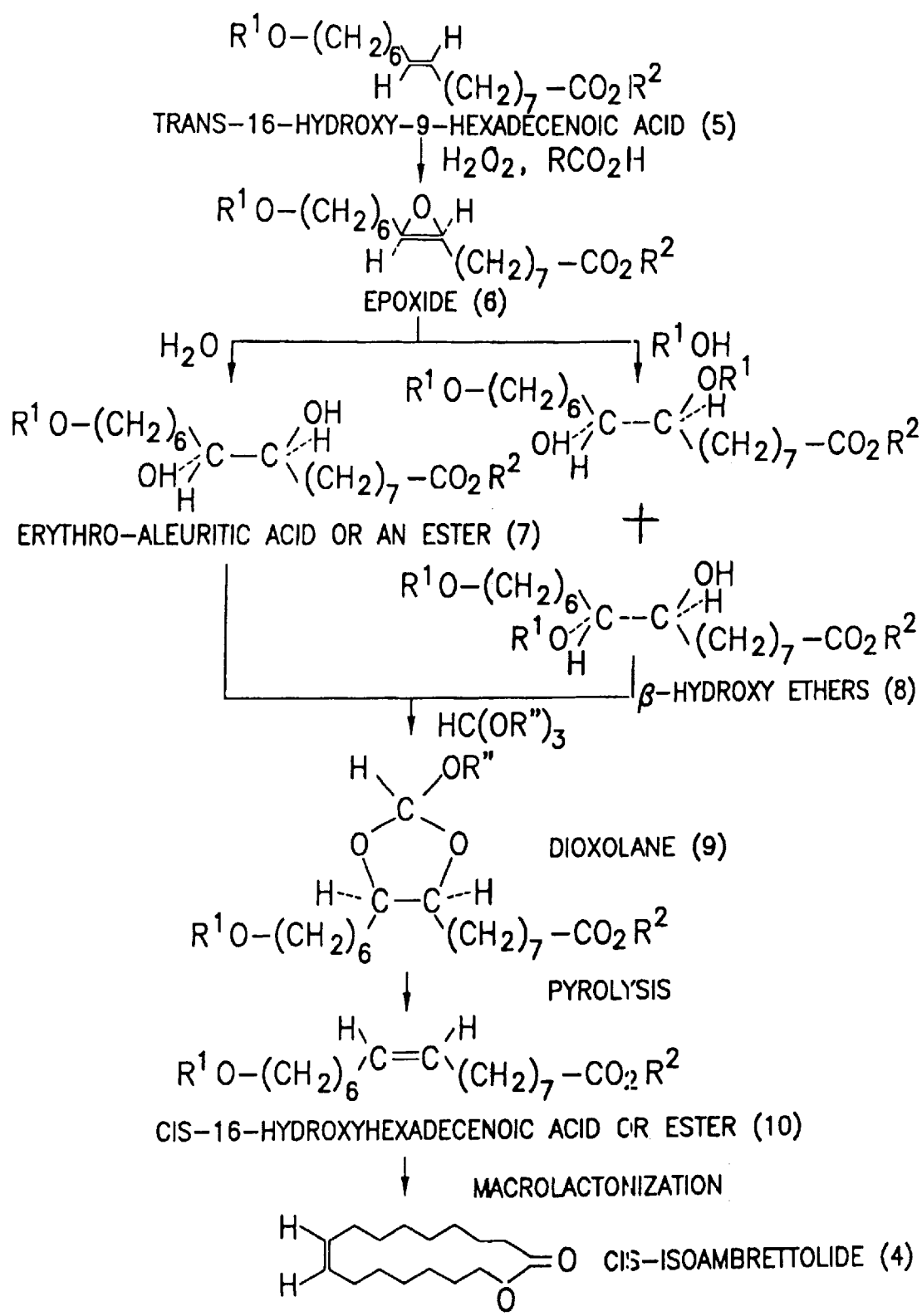
FIG. 1 represents the various steps in the process for manufacturing cis-isoambrettolide.

The set of steps in the manufacturing process is represented in FIG. 1.

Figure 2:
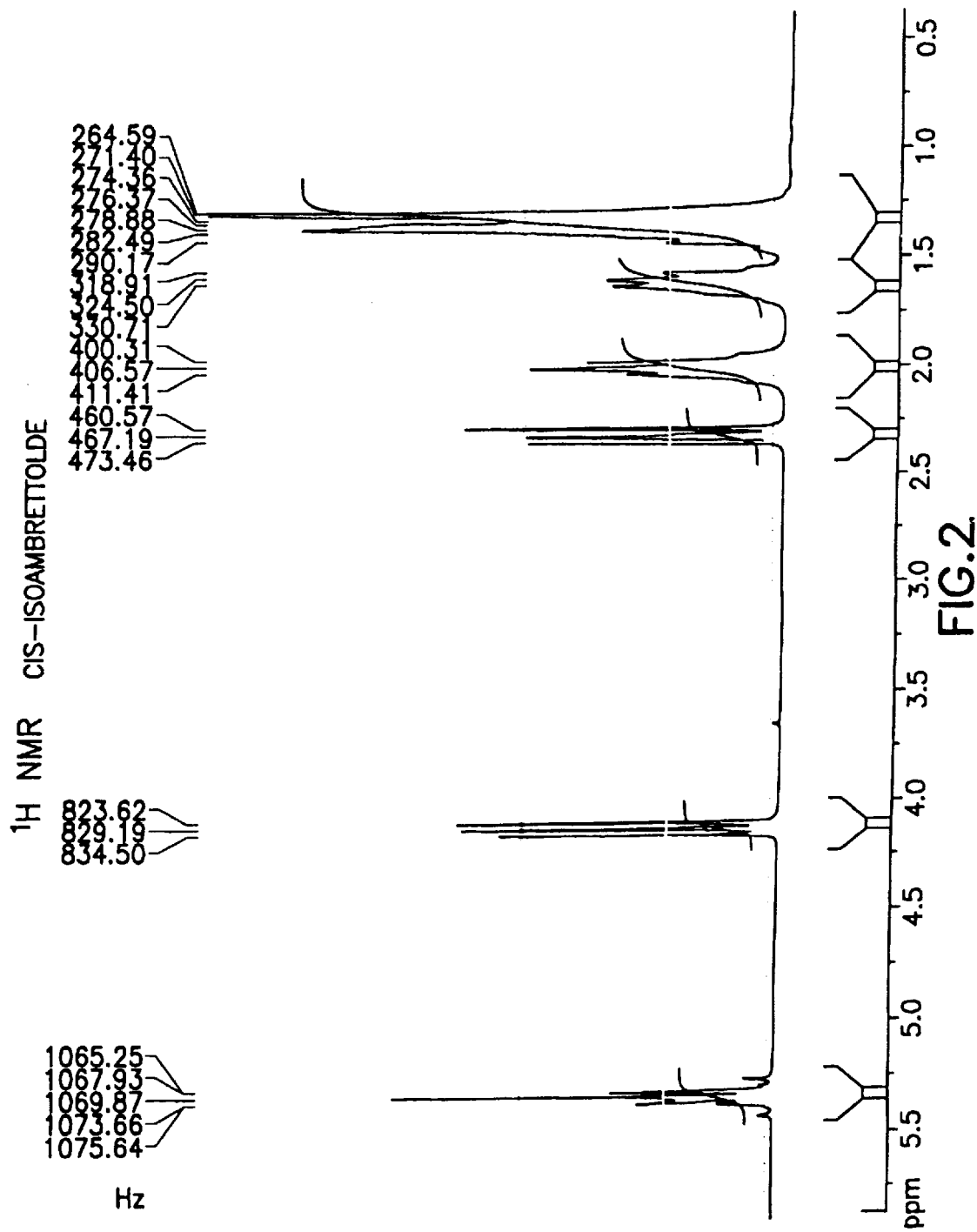
FIG. 2 represents the $^1H$ NMR spectrum of cis-isoambrettolide.
Figure 3:
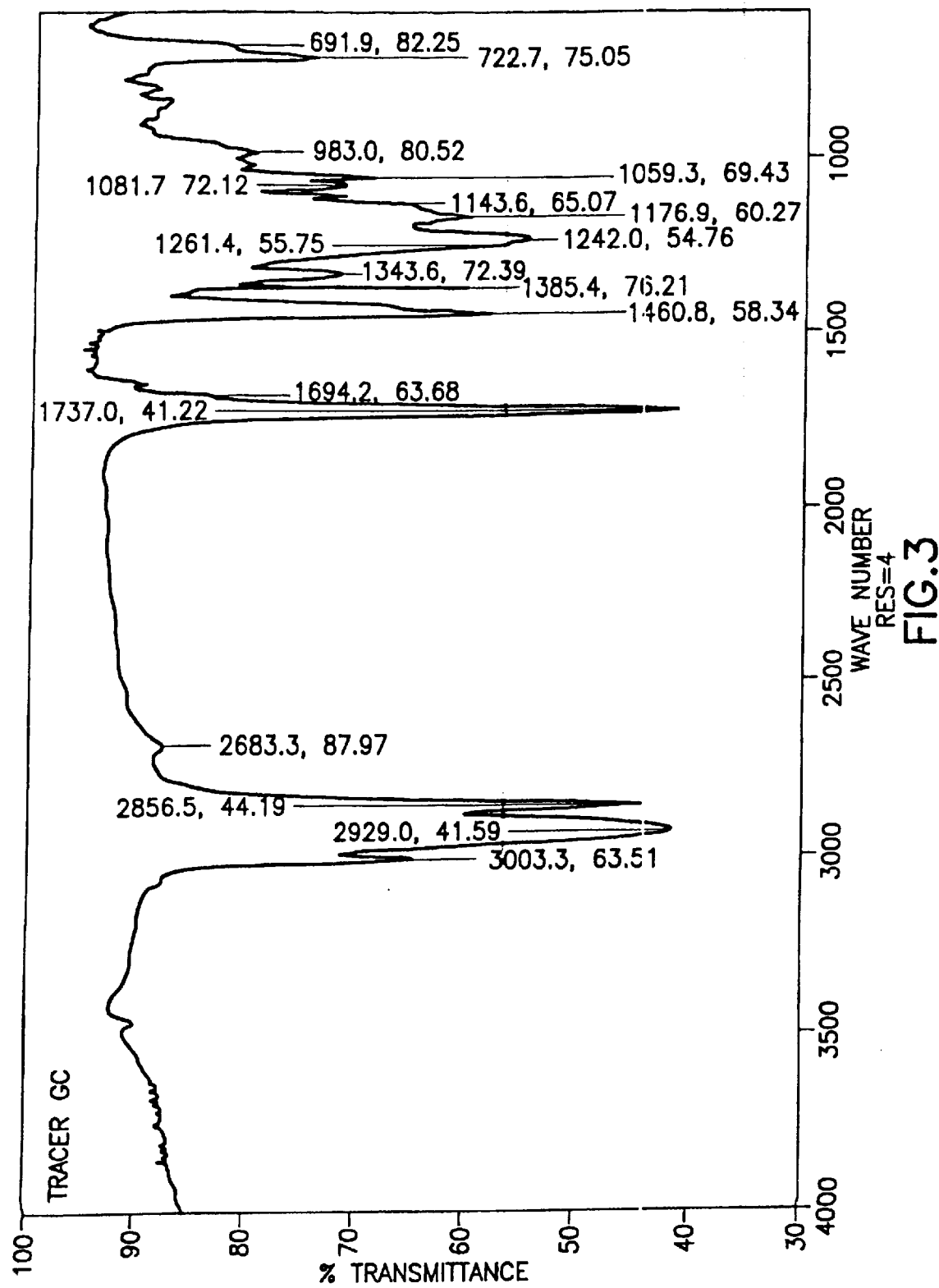
FIG. 3 represents the IR spectrum of cis-isoambrettolide.

The structure of the cis-isoambrettolide was confirmed by proton nuclear magnetic resonance spectroscopy and by infrared spectroscopy, as can be seen in FIGS. 2 and 3 respectively, the results of which are given below:

$^1$H NMR analysis of cis-isoambrettolide—solvent: $CDCl_3$

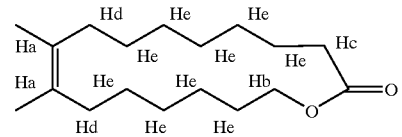

| H | δ (ppm) | integration | |
|---|---|---|---|
| Ha | 5.34 | 2 | Ha—Ha coupling: 8.06 Hz |
| Hb | 4.12 | 2 | |
| Hc | 2.34 | 2 | |
| Hd | 2.03 | 4 | |
| He | 1.34 to 1.6 | 18 | |

Analysis of the infrared absorption spectrum

The significant absorption bands are at about:

2929 $cm^{-1}$; 2883 $cm^{-1}$; 1737 $cm^{-1}$ and 1460 $cm^{-1}$

The round, musk, highly extended note of cis-isoambrettolide makes it a highly advantageous starting material in perfumery.

It gives any perfumery composition the development of the note, its diffusion, its roundness and its long-lasting nature without denaturing the note as a whole. This effect is perceptible from low doses, under 0,1%, and very pronounced for doses of from 1.5% to 5%.

A number of examples of compositions for perfumes or perfumed articles such as eaux de toilette, creams, lotions, soaps, detergents and aerosols using cis-isoambrettolide will be found below.

EXAMPLE 1

Thus, it is used in a floral feminine note of jasmine, violet, ylang nature according to the formula below: (parts by weight)

| | |
|---|---|
| Benzyl acetate | 6.00 |
| Styrallyl acetate | 0.50 |
| Cinnamyl alcohol | 1.20 |
| Phenylethyl alcohol | 16.00 |
| Undecylenic aldehyde at 10% | 1.30 |
| Hexylcinnamic aldehyde | 3.50 |
| Defurocoumarinized bergamot | 2.50 |
| Citronellol | 0.80 |
| Eugenol | 0.50 |
| Hedione | 0.70 |
| Hydroxycitronellal | 4.00 |
| Ionone | 1.00 |
| Irisarome | 7.00 |
| Isobornylcyclohexanol | 2.50 |
| cis-Jasmone at 10% | 0.50 |
| Linalool | 6.00 |
| Lyral | 1.00 |
| Methyl cedryl ketone | 2.00 |
| Methylisoeugenol | 2.00 |
| Amyl salicylate | 2.00 |
| Benzyl salicylate | 7.50 |
| Terpineol | 3.50 |
| Vetiverol | 2.00 |

-continued

| | |
|---|---|
| Ylang-ylang | 3.00 |
| cis-Isoambrettolide | 2.00 |
| | 79.00 |

The cis-isoambrettolide gives the note more development a rounder, more sophisticated note and musky and powdery long-lasting effect.

EXAMPLE 2

It is also used in a fresh, citriesydi, woody, ambery note for a unisex or masculine eau de toilette according to the formula below: (parts by weight)

| | |
|---|---|
| Acetal Bois 12 | 7.40 |
| Cedrenyl acetate | 1.20 |
| Isobornyl acetate | 2.50 |
| Linalyl acetate | 3.00 |
| Styrallyl acetate | 0.50 |
| Adoxal at 10% | 0.25 |
| Mandarin aldehyde at 10% | 0.25 |
| Allyl amyl glycolat | 0.60 |
| Ambrox at 10% | 2.50 |
| Calone 161 at 10% | 0.30 |
| L-carvone at 10% | 1.50 |
| Lemon oil | 8.40 |
| Cyclogalbanate | 0.40 |
| alpha Damascona at 10% | 4.00 |
| Citral diethyl acetal | 1.20 |
| Dimethylcyclohexenecarbaldehyde at 10% | 1.80 |
| Ethyllinalool | 8.00 |
| ethyltrimethylcyclopentenyl at 10% | 1.20 |
| Evernyl | 0.30 |
| Hedione | 10.00 |
| Helional | 1.70 |
| Hydroxycitronellal | 0.70 |
| Jessemal at 10% | 2.00 |
| Lavendin oil | 3.00 |
| Mandarin oil | 1.00 |
| Mentha citrata oil | 0.10 |
| Gamma Methylionone | 0.50 |
| Orange oil | 5.00 |
| cis-Isoambrettolide | 6.00 |
| | 75.30 |

The cis-isoambrettolide gives a musky character and develops the entire note and most particularly its citrusy aspect, its long-lastingness and its freshness.

These same results of development of the note, of its long-lastingness and of the fresh notes with a more sophisticated effect, are found in the fragrance compounds intended mainly for cosmetic preparation, for toiletries, for shampoos and hair products.

EXAMPLE 3

The use of cis-isoambrettolide is also very efficient in fragrance compounds intended for soaps, detergents, household cleaners and fabric softeners.

Thus, in the formula below, with a fresh, long-lasting note and a fruity aspect: (parts by weight)

| | |
|---|---|
| Para-tert-butylcyclohexyl acetate | 6.00 |
| Dimethylbenzylcarbinyl acetate | 0.70 |

-continued

| | |
|---|---|
| cis-3-Hexenyl acetate | 0.05 |
| Styrallyl acetate | 2.50 |
| Verdyl acetate | 4.00 |
| Phenethyl alcohol | 1.00 |
| Hexylcinnamic. aldehyde | 10.00 |
| Algix at 20% | 6.00 |
| Ambroxan at 10% | 1.00 |
| Methylmethoxyphenylpropanol | 0.60 |
| Cerinthol | 1.00 |
| Cetone Alpha | 2.00 |
| Dihydroionone Delta | 4.00 |
| Dihydromyrcenol | 7.30 |
| Eugenol | 0.20 |
| Floropal | 1.80 |
| Geraniol | 1.00 |
| Geranyl nitrile | 0.50 |
| Hedione | 10.00 |
| cis-3-Hexenol | 0.15 |
| Menthol | 0.30 |
| Methyl cedryl ketone | 10.00 |
| Gamma Methylionone | 4.60 |
| Nonadienal 2-6 DEA at 1% | 1.00 |
| Orange oil | 4.50 |
| cis-3-Hexenyl salicylate | 1.00 |
| Undecalactone | 10.00 |
| cis-Isoambrettolide | 15.00 |
| | 106.20 |

The cis-isoambrettolide develops the fresh note of this composition throughout the evaporation of the product and its long-lastingness and substantivity and develops a musky note.

Although the present description of the invention has been made with reference to specific embodiments, it is clear that various minor procedural modifications, which are within the immediate scope of a person skilled in the art, can be made without, however, departing from the scope of the invention as described and claimed.

Key for figures:
FIG. 1
trans-16-hydroxy-9-hexadecenoic acid (5)
epoxide (6)
erythro-aleuritic acid or an ester (7)
β-hydroxy ethers (8)
dioxolane (9)
pyrolyse→pyrolysis
cis-16-hydroxyhexadecenoic acid or ester (10)
macrolactonisation→macrolactonization
(4) remains unaltered
FIG. 2 (Title)
¹H NMR CIS-ISOAMBRETTOLIDE
FIG. 3
Horizontal axis to read:
Wave number
RES=4

What is claimed is:

1. A process for manufacturing cis-isoambrettolide comprising:
 (a) providing trans-16-hydroxy-9-hexadecenoic acid or acid ester having the formula:

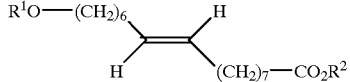

wherein $R^1$ is selected from the group consisting of hydrogen and an acetyl radical and $R^2$ is selected from the group consisting of hydrogen and a methyl radical;

(b) contacting said acid or acid ester with a mixture of a peroxide and a carboxylic acid to form the epoxide of the said acid or acid ester;

(c) subjecting said epoxide to hydrolysis in the presence of an acidic or basic medium to form erythro-aleuritic acid or acid ester;

(d) heating said acid or acid ester in the presence of an ortho ester having the formula $HC(OR^3)_3$, where $R^3$ is selected from the group consisting of a methyl and ethyl radical, to form the dioxolane;

(e) subjecting said dioxolane to pyrolysis treatment in the presence or absence of organic solvent to form cis-16-hydroxyhexadecenoic acid or acid ester having the formula:

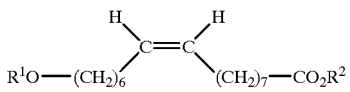

and, (f) subjecting the acid or acid ester product from step (e) to macrolactonization conditions.

2. A process for manufacturing cis-isoambrettolide comprising:

(a) providing trans-16-hydroxy-9-hexadecenoic acid or acid ester having the formula:

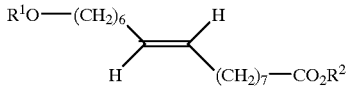

wherein $R^1$ is selected from the group consisting of hydrogen and an acetyl radical and $R^2$ is selected from the group consisting of hydrogen and a methyl radical;

(b) contacting said acid or acid ester with a mixture of a peroxide and a carboxylic acid to form the epoxide of said acid or acid ester;

(c) subjecting said epoxide to alcoholysis in the presence of an R'OH alcohol, wherein R' is selected from the group consisting of a methyl and ethyl radicals, to form a mixture of beta-hydroxy ethers;

(d) heating said ether mixture in the presence of an ortho ester having the formula $HC(OR^3)_3$, where $R^3$ is selected from the group consisting of a methyl and ethyl radical, to form the dioxolane;

(e) subjecting said dioxolane to pyrolysis treatment in the presence or absence of organic solvent to form cis-16-hydroxyhexadecenoic acid or acid ester having the formula:

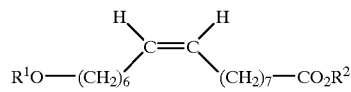

and, (f) subjecting the acid or acid ester product from step (e) to macrolactonization conditions.

3. The process of claim 1 wherein said peroxide in step (b) is hydrogen peroxide.

4. The process of claim 1 wherein said carboxylic acid in step (b) is selected from the group consisting of formic acid and acetic acid.

5. The process of claim 1 wherein said hydrolysis in step (c) is conducted in a basic medium.

6. The process of claim 1 wherein said hydrolysis in step (c) is conducted in an acid medium.

7. The process of claim 1 wherein said pyrolysis step (e) is conducted in the presence of an organic solvent.

8. The process of claim 1 wherein said pyrolysis step (e) is conducted in the absence of solvent.

9. The process of claim 1 wherein $R^1$ and $R^2$ are each hydrogen.

10. The process of claim 2 wherein said peroxide in step (b) is hydrogen peroxide and said carboxylic acid is selected from the group consisting of formic acid and acetic acid.

11. The process of claim 1 wherein the product from step (e) is recovered at a purity of greater than 99%.

12. The process of claim 1 wherein said cis-isoambrettolide is obtained in a geometrical isomer purity of greater 99.5%.

13. The process of claim 2 wherein said pyrolysis step in step (e) is conducted in the presence of organic solvent.

14. The process of claim 2 wherein said pyrolysis step in step (e) is conducted in the absence of solvent.

15. The process of claim 2 wherein $R^1$ and $R^2$ are each hydrogen.

16. The process of claim 2 wherein said cis-isoambrettolide is obtained in a geometrical isomer purity of greater than 99.5%.

* * * * *